US00PP21783P2

(12) United States Plant Patent
Smith

(10) Patent No.: US PP21,783 P2
(45) Date of Patent: Mar. 15, 2011

(54) *CHRYSANTHEMUM* PLANT NAMED 'YOGIGI SNOW'

(50) Latin Name: *Chrysanthemum×morifolium*
Varietal Denomination: Yogigi Snow

(75) Inventor: Mark A. Smith, Fort Myers, FL (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/592,050

(22) Filed: Nov. 18, 2009

(51) Int. Cl.
*A01H 5/00* (2006.01)

(52) U.S. Cl. ..... Plt./288

(58) Field of Classification Search ..... Plt./288
See application file for complete search history.

(56) References Cited

U.S. PATENT DOCUMENTS

PP16,677 P2 * 6/2006 Boeder ..... Plt./288
PP20,435 P2 * 10/2009 Wain ..... Plt./288

OTHER PUBLICATIONS

UPOV ROM GTITM Computer Database, GTI Jouve Retreival Software 2010/.*

* cited by examiner

*Primary Examiner*—Wendy Haas
(74) *Attorney, Agent, or Firm*—S. Matthew Edwards

(57) ABSTRACT

A new *Chrysanthemum* plant named 'Yogigi Snow,' particularly distinguished by the small white flowers with strong stiff plants, short, compact and mounded plant habit with a natural flowering season about the middle of September.

1 Drawing Sheet

Latin name of the genus and species of the plant claimed: *Chrysanthemum×morifolium.*

Varietal denomination: 'Yogigi Snow'.

BACKGROUND OF THE NEW PLANT

The present invention comprises a new *Chrysanthemum*, botanically known as *Chrysanthemum×morifolium*, and hereinafter referred to by the variety name 'Yogigi Snow.'

'Yogigi Snow' is a product of a planned breeding program. The new cultivar has small white flowers with strong stiff plants, short, compact and mounded plant habit with a natural flowering season about the middle of September.

'Yogigi Snow' originates as a natural whole plant mutation of 'Yogigi White,' U.S. Plant Pat. No. 20,435, and was discovered and selected by the inventor as a single flowering plant within a population of the parent cultivar in a controlled breeding program in Alva, Fla., in April 2007. The parent cultivar 'Yogigi White' has wider ray florets, shorter peduncles, and a couple days slower flowering response time.

The first act of asexual reproduction of 'Yogigi Snow' was accomplished when vegetative cuttings were propagated from the initial selection in April 2007 in a controlled environment in Alva, Fla.

BRIEF SUMMARY OF INVENTION

Horticultural examination of plants grown from cuttings of the plant initiated in April 2007, and continuing thereafter, has demonstrated that the combination of characteristics as herein disclosed for 'Yogigi Snow' are firmly fixed and are retained through successive generations of asexual reproduction.

'Yogigi Snow' has not been observed under all possible environmental conditions. The phenotype may vary significantly with variations in environment such as temperature, light intensity and day length.

Plant Breeder's Rights for this cultivar were applied for in the European Union on Nov. 26, 2008 and in Canada on Oct. 30, 2009. 'Yogigi Snow' has not been made publicly available more than one year prior to the filing of this application.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawing shows typical flower and foliage characteristics of 'Yogigi Snow' with colors being as true as possible with an illustration of this type. The photographic drawing shows a flowering potted plant of the new variety, and a close-up of the flowers.

DETAILED BOTANICAL DESCRIPTION

The plant descriptions, measurements and aforementioned photographs were taken outdoors in Gilroy, Calif. in late October 2009. These plants were approximately 12-14 weeks of age. The plants were propagated in Alva, Fla., then shipped to California at about 3-4 weeks of age, potted up and set outdoors in a trial.

Color references are made to The Royal Horticultural Society Colour Chart (R.H.S.) 2001.

TABLE 1

DIFFERENCES BETWEEN THE NEW VARIETY 'YOGIGI SNOW' AND A SIMILAR VARIETY

| | 'Yogigi Snow' | 'Crete' (U.S. Plant Pat. No. 16,677) |
|---|---|---|
| Inflorescence shape: | Rounder, more pom form | Flatter, more decorative form |

TABLE 1-continued

DIFFERENCES BETWEEN THE NEW VARIETY 'YOGIGI SNOW' AND A SIMILAR VARIETY

| | 'Yogigi Snow' | 'Crete' (U.S. Plant Pat. No. 16,677) |
|---|---|---|
| Plant habit: | More mound/less ball | More ball |
| Plant size: | Smaller | A bit larger |
| Branches: | Stronger/stiffer | Bit weaker/more flexible |

Plant:

*Form, growth and habit.*—Herbaceous decorative garden-type. Stems upright and outwardly spreading on short, mounded and compact plants, with strong and stiff branches.

*Plant height.*—5-7 cm.

*Plant height (inflorescence included).*—9-10 cm.

*Plant width.*—19-20 cm.

*Garden performance and tolerance to weather.*—Very good.

*Crop time to flowering.*—About 8-10 weeks.

Roots:

*Number of days to initiate roots.*—4 days at about 22 degrees C.

*Number of days to produce a rooted cutting.*—7-10 days at 22 degrees C.

*Type.*—Fine, fibrous, free branching.

*Color.*—RHS N155B but whiter.

Foliage:

*Arrangement.*—Alternate.

*Immature, leaf color, upper surface.*—Closest to RHS 147A.

*Immature, leaf color, lower surface.*—Closest to RHS 146A.

*Mature, leaf color, upper surface.*—Closest to RHS 146A.

*Mature, leaf color, lower surface.*—Closest to RHS 146B.

*Length.*—1.8-2.0 cm.

*Width.*—1.2-1.6 cm.

*Shape.*—Ovate.

*Base shape.*—Attenuate.

*Apex shape.*—Acute to mucronulate.

*Margin.*—Palmately lobed; irregularly incised and serrate.

*Texture, upper surface.*—Bifid T-shaped hairs.

*Texture, lower surface.*—Bifid T-shaped hairs.

*Color of veins, upper surface.*—Between RHS 146A and RHS 146B.

*Color of veins, lower surface.*—Between RHS 146A and RHS 146B.

*Petiole color.*—Between RHS 146A and RHS 146B.

*Length.*—0.5-0.7 cm.

*Diameter.*—0.2 cm.

*Texture.*—Bifid T-shaped hairs.

Stem:

*Quantity of main branches per plant.*—About 10.

*Quantity of leaves per branch.*—About 6-8.

*Color of stem.*—Between RHS 144B and 144C.

*Length of stem.*—5.5-6.5 cm.

*Diameter.*—0.3-0.35 cm.

*Length of internodes.*—0.5-0.8 cm.

*Texture.*—Bifid T-shaped hairs.

*Color of peduncle.*—Between RHS 147A and RHS 146B, but appears lighter because of so many hairs.

*Length of peduncle.*—3.5-4.5 cm.

*Peduncle diameter.*—0.1-0.15 cm.

*Texture.*—Bifid T-shaped hairs.

Inflorescence:

*Type.*—Composite type, solitary inflorescences (decorative-type) borne terminally above foliage, ray florets arranged acropetally on a capitulum.

*Blooming habit.*—Natural season flowering about the middle of September.

*Quantity of inflorescences per plant.*—45-50 open flowers and 15-20 buds.

*Quantity of inflorescences per lateral stem.*—6-7.

*Lastingness of individual blooms on the plant.*—About 4 weeks.

*Fragrance.*—Slightly spicy.

Bud (just before opening/showing color):

*Color.*—RHS 10C.

*Length.*—0.6-0.8 cm.

*Width.*—0.9-1.1 cm.

*Shape.*—Oblate.

Immature inflorescence:

*Diameter.*—2.5-3.0 cm.

*Color of ray florets, upper surface.*—Between RHS 4C and RHS 4D.

*Color of ray florets, lower surface.*—RHS 4D.

Mature inflorescence:

*Diameter.*—3.4-3.6 cm.

*Depth.*—1.0 cm.

*Total diameter of 'disc'.*—0.3-0.4 cm.

*Receptacle height.*—0.35 cm.

*Receptacle diameter.*—0.4 cm.

Ray florets:

*Average quantity of florets.*—140 in numerous whorls.

*Color of florets, upper surface.*—RHS 4D maturing to RHS 155D but whiter.

*Color of florets, lower surface.*—RHS 155D becoming white upon maturation.

*Length.*—1.5-1.6 cm.

*Width.*—0.5-0.6 cm.

*Shape.*—Elliptical.

*Apex shape.*—Praemorse.

*Margin.*—Entire.

*Texture, upper surface.*—Papillose.

*Texture, lower surface.*—Papillose.

Disc florets:

*Average quantity of florets.*—10-20.

*Color of florets.*—RHS 1C with RHS 17B apex.

*Length.*—0.4 cm.

*Width.*—0.1 cm.

*Shape.*—Tubular, elongated.

*Apex shape.*—Acute, 5 pointed.

Phyllaries:

*Quantity.*—About 25 in 2-3 whorls.

*Color, upper surface.*—RHS 146C.

*Color, lower surface.*—RHS 146A.

*Length.*—0.4-0.6 cm.

*Width.*—0.1-0.15 cm.

*Shape.*—Lanceolate.

*Apex shape.*—Acute.

*Based.*—Fused.

*Margins.*—Entire with a slight papery margin.

*Texture, upper surface.*—Glabrous.

*Texture, lower surface.*—Bifid T-shaped hairs.

Reproductive organs:

*Pistil.*—1.

*Length.*—0.5-0.6 cm.

*Style color.*—RHS 1C.

*Style length.*—0.3-0.4 cm.

*Stigma color.*—RHS 1A.

*Stigma shape.*—Bi-parted.

*Ovary color.*—RHS 155C.

*Stamens.*—1.

*Color of filaments.*—RHS 2D.

*Length filaments.*—0.2 cm.

*Anther color.*—RHS 17B.

*Anther length.*—0.15 cm.

*Anther shape.*—Oblong.

*Color of pollen.*—RHS 17C.

*Pollen amount.*—Moderate.

*Fertility/seed set.*—Has not been observed on this hybrid.

Disease/pest resistance: Has not been observed on this hybrid.

What is claimed is:

1. A new and distinct variety of *Chrysanthemum* plant named 'Yogigi Snow,' substantially as illustrated and described herein.

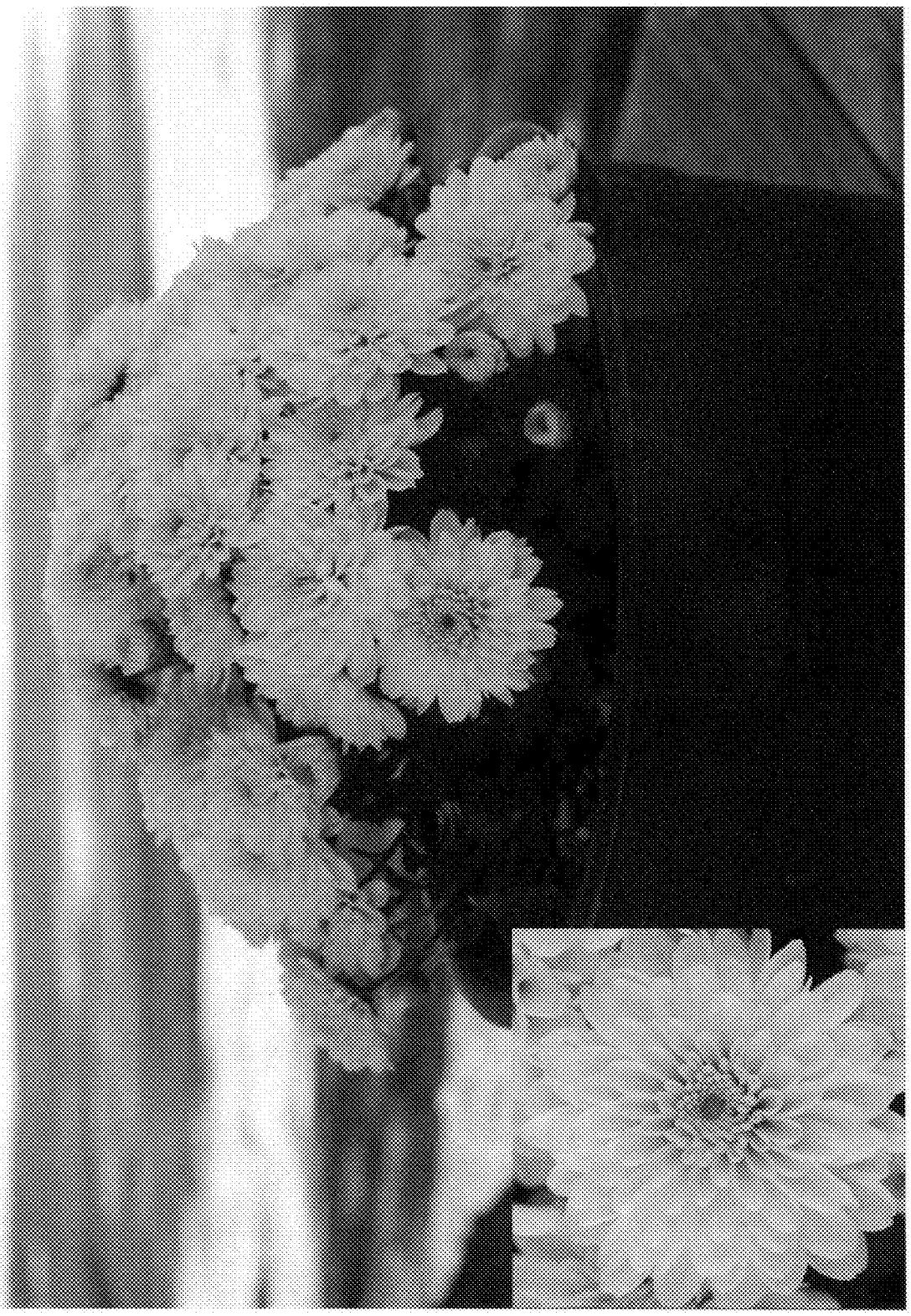

* * * * *